(12) United States Patent
Anand et al.

(10) Patent No.: US 11,686,738 B2
(45) Date of Patent: Jun. 27, 2023

(54) METHODS, SYSTEMS AND SOLID COMPOSITIONS FOR REAGENT DELIVERY

(71) Applicant: Ventana Medical Systems, Inc., Tucson, AZ (US)

(72) Inventors: Anisha Anand, Indianapolis, IN (US); Crystal L. Stephens, Tucson, AZ (US); Natcha Suriyavirun, Urbana, IL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 17/449,222

(22) Filed: Sep. 28, 2021

(65) Prior Publication Data

US 2022/0082579 A1    Mar. 17, 2022

Related U.S. Application Data

(60) Division of application No. 16/442,354, filed on Jun. 14, 2019, now Pat. No. 11,162,961, which is a
(Continued)

(51) Int. Cl.
*G01N 1/00*     (2006.01)
*G01N 35/00*    (2006.01)
(Continued)

(52) U.S. Cl.
CPC ......... *G01N 35/00029* (2013.01); *G01N 1/30* (2013.01); *G01N 1/31* (2013.01);
(Continued)

(58) Field of Classification Search
None
See application file for complete search history.

(56) References Cited

U.S. PATENT DOCUMENTS

| 4,673,654 A | 6/1987 | Talmage |
| 5,141,855 A | 8/1992 | Schmittou |

(Continued)

FOREIGN PATENT DOCUMENTS

| CN | 102597740 A | 7/2012 |
| EP | 0277723 A1 | 8/1988 |

(Continued)

OTHER PUBLICATIONS

International Bureau on Behalf of the International Searching Authority, International Preliminary Report on Patentability for International Patent Application No. PCT/US2017/067835 (dated Jun. 25, 2019).

(Continued)

*Primary Examiner* — Jyoti Nagpaul
(74) *Attorney, Agent, or Firm* — Charney IP Law LLC; Thomas M. Finetti

(57) ABSTRACT

Methods, systems, and compositions featuring a solid, dissolvable reagent composition for delivering the reagent, such as an antibody, probe, chromogen, etc., to a sample. The present invention also features methods of producing said compositions, and automated systems featuring the use of the solid, dissolvable reagent compositions. The solid, dissolvable reagent composition may comprise a water-soluble polymer film, such as a polyvinyl alcohol film, infused with the reagent, wherein when applied to the sample, the water-soluble polymer film with reagent contacts the sample (e.g., tissue) and dissolves.

9 Claims, 5 Drawing Sheets
(5 of 5 Drawing Sheet(s) Filed in Color)

Related U.S. Application Data continuation of application No. PCT/US2017/067835, filed on Dec. 21, 2017.

(60) Provisional application No. 62/437,545, filed on Dec. 21, 2016.

(51) Int. Cl.
  G01N 1/30 (2006.01)
  G01N 1/31 (2006.01)
  G01N 33/68 (2006.01)
  G01N 33/53 (2006.01)

(52) U.S. Cl.
  CPC ............ G01N 1/312 (2013.01); G01N 33/53 (2013.01); G01N 33/6854 (2013.01); G01N 35/00 (2013.01); *G01N 2474/20* (2021.08)

(56) References Cited

U.S. PATENT DOCUMENTS

| | | | |
|---|---|---|---|
| 5,171,669 A | 12/1992 | Burdick et al. | |
| 5,182,216 A | 1/1993 | Clayton et al. | |
| 5,403,706 A | 4/1995 | Wilk et al. | |
| 5,965,454 A | 10/1999 | Farmilo et al. | |
| 6,309,893 B1 | 10/2001 | Deeley et al. | |
| 2011/0256549 A1* | 10/2011 | Gaylord | H01L 51/0043 562/466 |
| 2011/0305768 A1 | 12/2011 | Mao et al. | |

FOREIGN PATENT DOCUMENTS

| | | |
|---|---|---|
| EP | 0299359 A2 | 1/1989 |
| EP | 0299878 A1 | 1/1989 |
| JP | S5248598 A | 4/1977 |
| JP | S56-22956 A | 3/1981 |
| JP | 62175196 A | 7/1987 |
| JP | 6382363 A | 4/1988 |
| JP | 64-55197 A | 3/1989 |
| JP | H0726961 B | 1/1995 |
| JP | 2002-533695 A | 10/2002 |
| JP | 2007-500363 A | 1/2007 |
| JP | 2013-040974 A | 2/2013 |
| JP | 2015-507189 A | 3/2015 |
| JP | 2015-509583 A | 3/2015 |
| WO | 96/09549 A1 | 3/1996 |
| WO | 0151909 A1 | 7/2001 |
| WO | 2004/111638 A1 | 12/2004 |
| WO | 00/38838 A1 | 7/2007 |
| WO | 2010/002418 A2 | 1/2010 |
| WO | 2011025442 A1 | 3/2011 |
| WO | 2013/110549 A1 | 8/2013 |
| WO | 20130119845 A1 | 8/2013 |
| WO | 2015/053393 A1 | 4/2015 |
| WO | 2016/170008 A1 | 10/2016 |

OTHER PUBLICATIONS

International Searching Authority, International Search Report for International Patent Application No. PCT/US2017/067835 (dated Jun. 28, 2018).

International Searching Authority, Written Opinion of the International Searching Authority for International Patent Application No. PCT/US2017/067835 (dated Jun. 28, 2018).

\* cited by examiner

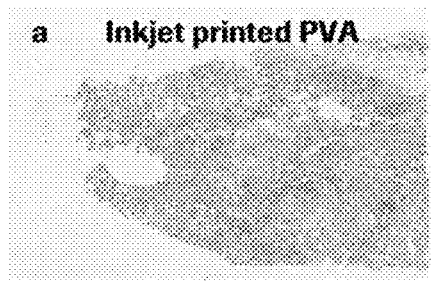
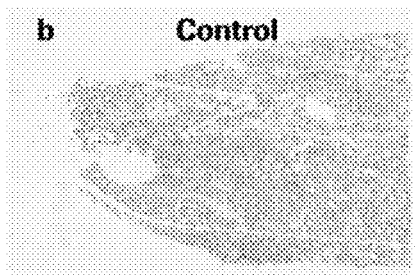
FIG. 11A  FIG. 11B
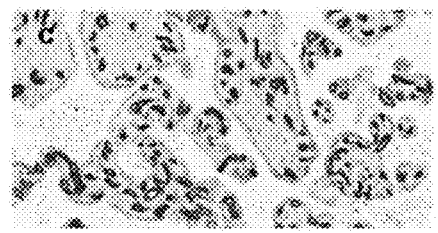
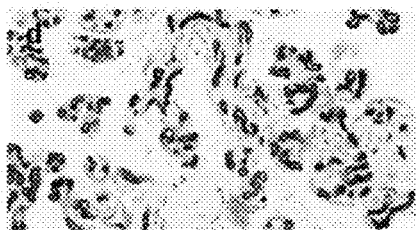
FIG. 11C  FIG. 11D

METHODS, SYSTEMS AND SOLID COMPOSITIONS FOR REAGENT DELIVERY

CROSS-REFERENCE TO RELATED APPLICATIONS

This patent application is a divisional patent application of U.S. patent application Ser. No. 16/442,354, filed Jun. 14, 2019, which is a continuation of International Patent Application No. PCT/US2017/067835, filed Dec. 21, 2017, which claims priority to and the benefit of U.S. Provisional Patent Application No. 62/437,545, filed Dec. 21, 2016. Each of the above patent applications is incorporated herein by reference as if set forth in their entireties.

FIELD OF THE INVENTION

The present disclosure relates to antibodies and reagent delivery, more particularly to methods, systems, and compositions for antibody delivery using solid compositions such as a solid, dissolvable single-dose antibody composition.

BACKGROUND OF THE INVENTION

Current reagent dispenser systems for automated cell stainers are generally produced to accommodate at least 50 tests, and the reagents generally have a limited shelf life (e.g., 9-24 months). Many reagents must be kept at 4° C. The dispensers are designed to deliver precise drops (e.g., 100 µL) of solutions (comprising antibodies, probes and/or other reagents) to target slides; however, mis-dispense and residue formation can potentially lead to inaccurate volumes of liquid being delivered and subsequent slide staining failures.

SUMMARY OF INVENTION

It was surprisingly discovered reagents, such as antibodies, could be incorporated into a water-soluble polymer (such as polyvinyl alcohol (PVA) such that the reagents were not degraded or destroyed. For example, as described below, antibodies were safely heated with PVA without causing damage to the functionality of the antibody, creating a solid, dissolvable reagent composition.

The present invention features compositions comprising a solid, dissolvable reagent composition for delivering said reagent (e.g., antibodies, probes, buffers, chromogens, counterstains, enzymes, nucleic acids, etc.) to a sample. The compositions comprise a water-soluble polymer (e.g., a film, a pouch, a wafer, etc.) and the reagent. In some embodiments, the reagent is infused, printed, embedded, or encapsulated in the water-soluble polymer. When the composition is applied to a sample, the water-soluble polymer contacts the sample and dissolves, allowing the reagent to contact the sample. A non-limiting example of a water-soluble polymer is polyvinyl alcohol (PVA).

In some embodiments, the reagent (e.g., antibody, probe, stain, enzyme, etc.) is infused between at least two layers of the water-soluble polymer film. In some embodiments, the reagent is inkjet-printed onto the surface of the water-soluble polymer film. In some embodiments, the reagent is embedded into the water-soluble polymer film.

The present invention also features methods of producing said compositions and methods of using said compositions (applications of the compositions), e.g., histochemical methods, methods of introducing antibodies to a sample, etc. The present invention also features systems (e.g., automated systems, manual systems) featuring the use of said compositions. For example, the present invention features methods, systems, and compositions for delivering antibodies, stains, or other reagents to a tissue sample adhered to a slide. The solid, dissolvable reagents of the present invention may be used in an automated staining machine. The present invention is not limited to automated methods and systems. In some embodiments, the compositions of the present invention are applied to a sample in a manual manner.

The sample may be of any type appropriate for the application. For example, in some embodiments, a tissue sample is an appropriate sample for histological examination on a slide. In one embodiment, the tissue sample may be immobilized on a slide and further processed with an automated slide stainer, for instance an automated IHC/ISH slide stainer. In some embodiments, the tissue sample may be taken from a biopsy or a surgical resection. The tissue sample may further comprise, for example, a section of a cancerous or healthy tissue. In addition, the tissue sample may be taken from a liquid cytology sample. Note the sample is not limited to a tissue sample.

The present invention is not limited to the specific steps, components, compositions, etc. For example, other water-soluble substrates may be used. Various different temperatures, humidity, or other conditions may be considered. Other reagents may be used, etc.

Without wishing to limit the present invention to any theory or mechanism, it is believed that the solid, dissolvable compositions (and methods and systems herein) are advantageous. For example, the composition may be kept at room temperature (even left on instruments for long periods of time) and that the composition may be more stable than the reagent in a liquid form. Other advantages may include the elimination of the need to rehydrate the reagent prior to application on the sample (bypass of a hydration step). The number of steps needed to perform certain experiments can be reduced. In the case of an automated system, the number of dispensers required is reduced. Further, one could perform small numbers of experiments (e.g., 1 slide, 5 slides) or large numbers (e.g., 50 slides).

Note the present invention also features compositions made from the water-soluble polymer (e.g., PVA) and reaction buffer (or other buffer) as an alternative to the water-soluble polymer (e.g., PVA) and water/ethanol.

The present invention provides an automated staining system comprising: a base for supporting a sample (e.g., a tissue section, a tissue sample); a liquid dispenser for aliquoting a liquid onto the sample on the base; and a solid composition for depositing onto the sample on the base. The solid composition dissolves onto the sample and thereby depositing the reagent on the sample. In some embodiments, when the solid composition contacts the sample, the composition dissolves thereby depositing the reagent on the sample. The solid composition may be deposited manually. In some embodiments, the solid composition is deposited in an automated manner. For example, in some embodiments, the system comprises a solid reagent dispenser for depositing the solid composition onto the sample. In some embodiments, the system comprises a holding container for storing or holding the solid composition. In some embodiments, the solid reagent dispenser retrieves a solid reagent from the holding container and moves it to the sample on the base.

In certain embodiments, the solid composition comprises a water-soluble polymer and a reagent embedded therein, the reagent is selected from a group consisting of: an antibody, an antibody fragment, a protein, a nucleic acid, a chromogen, a stain, a counterstain, a lipid, a carbohydrate, an enzyme, a buffer, or a combination thereof; the solid composition is deposited on the sample manually.

In some embodiments, the liquid dispenser aliquots the liquid onto the sample on the base before the solid composition is deposited onto the sample on the base. In some embodiments, the liquid dispenser aliquots the liquid onto the sample on the base after the solid composition is deposited onto the sample on the base.

The system may be capable of holding and processing multiple slides. For example, in some embodiments, the system holds and processes at least 20 samples. In some embodiments, the system holds and processes at least 50 samples. The automated staining system may for introducing a stain to the sample. In some embodiments, the system may be for performing a histochemistry assay on the sample. In some embodiments, the system may be for performing in situ hybridization on the sample. In some embodiments, the system may be for automated DNA amplification or sequencing.

In certain embodiments, the system can deliver solid compositions or both solid and liquid compositions to the sample.

In certain embodiments, the system further comprises an image acquisition system, an image analysis system, or both an image acquisition system and image analysis system.

In some embodiments, the water-soluble polymer comprises polyvinyl alcohol (PVA), dextran, hydroxypropyl cellulose, poly (acrylic acid sodium salt), poly (ethylene glycol), poly (methylacrylic acid sodium salt), poly(styreneslfonic acid sodium salt), pullulan, or a combination thereof. In some embodiments, the composition comprises two or more reagents. In some embodiments, the water-soluble polymer is a film. In some embodiments, the reagent is embedded or infused in the water-soluble polymer. In some embodiments, the reagent is printed on the water-soluble polymer. In some embodiments, the reagent is encapsulated by the water-soluble polymer. In some embodiments, the reagent is encapsulated by two or more layers of the water-soluble polymer. In some embodiments, the solid composition further comprises salts from a buffer. In some embodiments, the solid composition further comprises a buffering agent. In some embodiments, the sample comprises a tissue sample, e.g., a tissue section. In some embodiments, the sample is mounted on a slide.

The present invention also provides a method of depositing a reagent onto a sample. In some embodiments, the method comprises: in a system comprising a base for supporting a sample and a liquid dispenser for aliquoting a liquid onto the sample on the base: placing a sample onto the base of the system; and depositing a solid composition onto the sample on the base, wherein when the solid composition contacts the sample, the composition dissolves thereby depositing the reagent on the sample. In some embodiments, the solid composition comprises a water-soluble polymer a reagent embedded therein, the reagent is selected from a group consisting of: an antibody, an antibody fragment, a protein, a nucleic acid, a chromogen, a stain, a counterstain, a lipid, a carbohydrate, an enzyme, a buffer, or a combination thereof.

In some embodiments, the solid composition is deposited on the sample manually. In some embodiments, the solid composition is deposited on the sample in an automated manner. In some embodiments, the system further comprises a holding container for holding the solid composition. In some embodiments, the system comprises a solid reagent dispenser for depositing the solid composition onto the sample. In some embodiments, the solid reagent dispenser retrieves a solid reagent from the holding container and moves it to the sample on the base.

In some embodiments, the liquid dispenser aliquots the liquid onto the sample on the base before the solid composition is deposited onto the sample on the base. In some embodiments, the liquid dispenser aliquots the liquid onto the sample on the base after the solid composition is deposited onto the sample on the base.

In certain embodiments, the system is capable of holding and processing multiple samples. For example, in some embodiments, the system can hold and process at least 20 samples. In some embodiments, the system can hold and process at least 50 samples.

In certain embodiments, the system is for introducing a stain to the sample. In some embodiments, the system is for performing a histochemistry assay on the sample. In some embodiments, the system is for performing in situ hybridization on the sample. In some embodiments, the system is for automated DNA amplification or sequencing.

In some embodiments, the system can deliver solid compositions or both solid and liquid compositions to the sample. In some embodiments, the system further comprises an image acquisition system, an image analysis system, or both an image acquisition system and image analysis system.

In certain embodiments, the water-soluble polymer comprises polyvinyl alcohol (PVA), dextran, hydroxypropyl cellulose, poly (acrylic acid sodium salt), poly (ethylene glycol), poly (methylacrylic acid sodium salt), poly(styreneslfonic acid sodium salt), pullulan, or a combination thereof. In some embodiments, the composition comprises two or more reagents. In some embodiments, the water-soluble polymer is a film. In some embodiments, the reagent is embedded or infused in the water-soluble polymer. In some embodiments, the reagent is printed on the water-soluble polymer. In some embodiments, the reagent is encapsulated by the water-soluble polymer. In some embodiments, the reagent is encapsulated by two or more layers of the water-soluble polymer. In some embodiments, the solid composition further comprises salts from a buffer. In some embodiments, the solid composition further comprises a buffering agent. In some embodiments, the sample comprises a tissue sample, e.g., a tissue section. In some embodiments, the sample is mounted on a slide.

The present invention provides an automated apparatus for delivering a reagent to a sample. In certain embodiments, the system comprises an automated machine for holding at least sample (e.g., a sample on a slide, e.g., a tissue sample mounted on a slide); a dispensing mechanism in the automated machine for placing a solid composition on the sample, wherein when the composition contacts the sample, the composition dissolves thereby depositing the reagent on the sample. The solid composition comprises a water-soluble polymer and a reagent selected from: an antibody, an antibody fragment, a protein, a nucleic acid, a chromogen, a stain, a counterstain, a lipid, a carbohydrate, an enzyme, a buffer, or a combination thereof.

The apparatus may comprise a holding container (e.g., in the automated machine, connected to the automated machine) holding the solid composition. The solid composition may be stored in the automated machine until dispensed onto the sample. In some embodiments, the solid composition is stored in a holding container.

In certain embodiments, the automated machine is an automated system such as those described herein for introducing a stain to a sample, for performing histochemical assays, for performing in situ hybridization, etc. For example, specific examples of automated staining machines (e.g., IHC/ISH slide stainers) include: itelliPATH (Biocare Medical), WAVE (Celerus Diagnostics), DAKO OMNIS and DAKO AUTOSTAINER LINK 48 (Agilent Technologies), BENCHMARK XT (Ventana Medical Systems, Inc.), BENCHMARK ULTRA (Ventana Medical Systems, Inc.), BENCHMARK GX (Ventana Medical Systems, Inc.), VENTANA H&E 600 (Ventana Medical Systems, Inc.), BENCHMARK Special Stains (Ventana Medical Systems, Inc.), VENTANA DISCOVERY XT (Ventana Medical Systems, Inc.), VENTANA DISCOVERY ULTRA (Ventana Medical Systems, Inc.), Leica BOND, and Lab Vision Autostainer (Thermo Scientific). Automated staining machines (automated slide stainers) are also described by Prichard, Overview of Automated Immunohistochemistry, Arch Pathol Lab Med., Vol. 138, pp. 1578-1582 (2014), incorporated herein by reference in its entirety. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. The methods of the present invention may be adapted to be performed on any appropriate automated staining machine (or automated slide processing machine).

In certain embodiments, the automated apparatus (e.g., automated machine) is for automated DNA or RNA amplification. In certain embodiments, the automated apparatus (e.g., automated machine) is for DNA sequencing.

The automated machine may be capable of holding and processing at least 20 samples. The automated machine may be capable of holding and processing at least 50 samples.

The apparatus (e.g., automated machine) may be configured with one or more dispensing mechanisms for delivering the solid composition to the sample, e.g., two or more dispensing mechanism, three or more, etc. The dispensing mechanism(s) may be able to deliver more than one solid composition (e.g., two or more different solid compositions) to the sample. The apparatus (e.g., automated machine) may be configured to deliver solid compositions to the sample. The apparatus may be configured to deliver both solid and liquid compositions to the sample.

In some embodiments, the apparatus further comprises image acquisition system, an image analysis system, or both an image acquisition system and image analysis system. One example of a brightfield imager that can generate digitized tissue data is the iScan HT and DP200 (Griffin) brightfield scanner sold by Ventana Medical Systems, Inc., or any microscope having one or more objective lenses and a digital imager, as well as a set of spectral filters. In some embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entirety. Other examples of commercially available slide scanners include: 3DHistech PANNORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. The present invention is not limited to the aforementioned image systems.

The present invention provides solid compositions comprising a water-soluble polymer and a reagent selected from: an antibody, an antibody fragment, a protein, a nucleic acid, a chromogen, a stain, a counterstain, a lipid, a carbohydrate, an enzyme, a buffer, or a combination thereof. In certain embodiments, the water-soluble polymer comprises polyvinyl alcohol (PVA), dextran, hydroxypropyl cellulose, poly (acrylic acid sodium salt), poly (ethylene glycol), poly (methylacrylic acid sodium salt), poly(styreneslfonic acid sodium salt), pullulan, or a combination thereof. In certain embodiments, the composition comprises two or more reagents.

In some embodiments, the water-soluble polymer is a film. In some embodiments, the reagent is embedded or infused in the water-soluble polymer. In some embodiments, the reagent is printed on the water-soluble polymer. In some embodiments, the reagent is encapsulated by the water-soluble polymer. In some embodiments, the reagent is encapsulated by two or more layers of the water-soluble polymer. In some embodiments, the solid composition further comprises salts from a buffer. In some embodiments, the solid composition further comprises a buffering agent.

The present invention also provides methods for contacting a sample with a reagent, wherein the method comprises applying to the sample a solid composition according to the present invention, wherein the composition dissolves upon contact with the sample thereby depositing the reagent on the sample. The sample may be a tissue sample, e.g., a tissue sample mounted on a slide. The method may feature placing the sample in an automated staining machine (e.g., as described above). The method may feature placing the sample in an automated apparatus (e.g., as described above).

The present invention also provides workflow methods for processing and preparing a sample and subjecting the sample to an automated method such as IHC or ISH on an automated staining machine using solid reagents (as described herein). For example, the method may comprise preparing tissue section from a tumor of a patient, e.g., sectioning a FFPE tissue sample of a tumor of a patient using a microtome and mounting the tissue section on a slide; histochemically staining the tissue section for a target biomarker, wherein one or more reagents used to stain the tissue section are solid reagents. The tissue section may be placed in an automated staining machine, which automatically dispenses one or more solid reagents onto the tissue section for the purpose of staining the target biomarker. The method may include staining the tissue section for a second target biomarker using one or more solid reagents in an automated staining machine.

The present invention also provides automated staining systems comprising at least one holding container for holding a solid reagent and an apparatus (e.g., a mechanical means, a dispensing arm) for obtaining a unit of the solid reagent from the holding container and placing the solid reagent on a slide.

The present invention also features histochemical methods for labeling a target biomarker in a tissue sample, wherein the methods comprise contacting the sample with a solid composition of the present invention to thereby introduce a reagent to the sample.

The present invention also features in situ hybridization methods for labeling a target nucleic acid in a tissue sample, wherein the methods comprise contacting the sample with a solid composition of the present invention to thereby introduce a reagent to the sample.

The present invention also features staining methods for staining a tissue sample, wherein the methods comprise contacting the sample with a solid composition of the present invention to thereby introduce a reagent to the sample.

The present invention also features nucleic acid (e.g., DNA, RNA) amplification methods for amplifying DNA, wherein the methods comprise contacting the sample with a solid composition of the present invention to thereby introduce a reagent to the sample for the purpose of amplifying nucleic acid.

The present invention also features nucleic acid (e.g., DNA, RNA) sequencing methods, wherein the methods comprise contacting the sample with a solid composition of the present invention to thereby introduce a reagent to the sample for the purpose of sequencing nucleic acid.

The present invention also features kits comprising one or more solid compositions. For example, a kit may comprise one or more of: a solid composition comprising a deparaffinization reagent, a solid composition comprising an antigen retrieval solution, a solid composition comprising a primary antibody, a solid composition comprising a secondary antibody, a solid composition comprising a third antibody, a solid composition comprising a first detection reagent, a solid composition comprising a second detection reagent, a solid composition comprising Hematoxylin, and a solid composition comprising a Bluing Reagent.

In certain embodiments, the kit may comprise reagents for histochemistry (e.g., immunohistochemistry). For example, in some embodiments, the kit may comprise one or more of: a solid composition comprising a deparaffinization reagent, a solid composition comprising an antigen retrieval solution, a solid composition comprising a specific binding agent for a target (e.g., an antibody), a solid composition comprising a detection reagent, a solid composition comprising a counterstain, a solid composition comprising a morphological stain, etc.

The kit may comprise reagents for staining, e.g., one or a combination of: a solid composition comprising a counterstain, a solid composition comprising a morphological stain, a solid composition comprising a chromogenic stain, etc.

Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4', 6-diamino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labeled phalloidin, (stains filamentous actin, color depends on conjugated fluorophore).

Many morphological stains are known, including but not limited to, hematoxylin and eosin (H&E) stain and Lee's Stain (Methylene Blue and Basic Fuchsin).

In certain embodiments, the kit may comprise reagents for in situ hybridization. For example, in some embodiments, the kit may comprise one or more of: a solid composition comprising a deparaffinization reagent, a solid composition comprising an antigen retrieval solution, a solid composition comprising a nucleic acid probe, a solid composition comprising a detection reagent, etc.

In certain embodiments, the kit comprises one or more detection reagents. Non-limiting examples of commercially available detection reagents or kits comprising detection reagents include: VENTANA ultraView detection systems (secondary antibodies conjugated to enzymes, including HRP and AP); VENTANA iVIEW detection systems (biotinylated anti-species secondary antibodies and streptavidin-conjugated enzymes); OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); OptiView Amplification system (Anti-species secondary antibody conjugated to a hapten, an anti-hapten tertiary antibody conjugated to an enzyme multimer, and a tyramide conjugated to the same hapten; VENTANA DISCOVERY (e.g. DISCOVERY Yellow Kit, Discovery Purple Kit, Discovery Silver kit, DISCOVERY Red Kit, DISCOVERY Rhodamine Kit, etc.) VENTANA DISCOVERY OmniMap, VENTANA DISCOVERY UltraMap anti-hapten antibody, secondary antibody, chromogen, fluorophore, and dye kits, each of which are available from Ventana Medical Systems, Inc. (Tucson, Ariz.); PowerVision and PowerVision+ IHC Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

In some embodiments, the automated apparatus (e.g., automated staining machine) can hold multiple solid compositions, e.g., solid compositions for each reagent involved in a particular assay, e.g., solid compositions for each reagent involved in a particular staining method, histochemistry method, in situ hybridization method, DNA amplification method, DNA sequencing method, etc.

Without wishing to limit the present invention to any theory or mechanism, it is believed that a discrete, single-dose delivery composition (and method) would have advantages, such as the potential to be more precise and reliable, the potential to improve stability and/or shelf life of the reagent (e.g. antibody), the simplification of an automated system (e.g., the instrument or dispenser would not be required to accurately measure out and deliver small volumes of liquid), etc. Additionally, such compositions and methods may appeal to low-throughput users such as those who do not have the run volume to utilize large amounts of rare or expensive reagents/assays before the expiration date. Users could potentially increase their range of assays if single-slide advanced staining kits and single-slide doses for rare and expensive reagents/assays were available. A solid delivery method may also reduce reagent waste. For example, in the case of an automated system, it would not be necessary to prime the dispensers before each run. Single-serving compositions may also increase the ease of use (e.g., the reagents can be kept at room temperature, all required reagents may be included in one dispenser, no need to ensure that all of the required reagents needed for an assay have been loaded onto the instrument, etc.) and reduce costs.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The application or application file contains at least one drawing executed in color. Copies of this patent or patent application publication with color drawing(s) will be provided by the Office upon request and payment of the necessary fee.

FIG. 11A is a micrograph illustrating normal placenta tissue stained with CD34 (QBEnd/10) primary antibody printed onto PVA film.

FIG. 11B is a micrograph illustrating normal placenta tissue stained with CD34 (QBEnd/10) primary antibody delivered with a dispenser as a control.

FIG. 11C is a micrograph illustrating 40× magnification of the slide of FIG. 11A.

FIG. 11D is a micrograph illustrating 40× magnification of the slide of FIG. 11B.

DETAILED DESCRIPTION OF THE INVENTION

Definitions

Figure 1A:
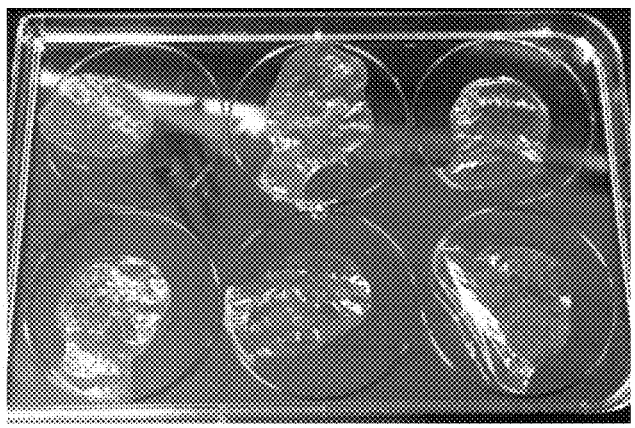
FIG. 1A shows distribution of reagent-PVA solutions in trays in 500 μL droplets for dehydration into a film in an oven at 37° C. for 1 hour.

The term "antibody" herein is used in the broadest sense and encompasses various antibody structures, including but not limited to monoclonal antibodies, polyclonal antibodies, multispecific antibodies (e.g., bispecific antibodies), and antibody fragments.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "monoclonal antibody" refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. The term "polyclonal antibody" refers to an antibody preparation that typically includes different antibodies directed against different determinants (epitopes). In contrast to a polyclonal antibody, each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is: characteristic of a particular disease state; indicative of the severity of a disease or the likelihood of disease progression or regression; and/or predictive that a particular disease state will respond to a particular treatment. As another example, the biomarker may be an infectious agent (such as a bacterium, fungus, virus, or other microorganism), or a substituent molecule or group of molecules thereof.

As used herein, the terms "sample" and "biological sample" shall refer to any composition containing or presumed to contain a biomarker or a composition being tested for the presence or absence of a particular biomarker. Samples may include purified or separated components of cells, tissues, or blood, e.g., DNA, RNA, proteins, cell-free portions, or cell lysates. The sample can be a formalin-fixed, paraffin-embedded (FFPE) tissue sample, e.g., from a tumor or metastatic lesion, e.g., primary tumor or metastatic tumor. The sample can also be from previously frozen or fresh tissue, or from a liquid sample, e.g., blood or a blood component (plasma or serum), urine, semen, saliva, sputum, mucus, semen, tear, lymph, cerebral spinal fluid, material washed from a swab, etc. Samples also may include constituents and components of in vitro cultures of cells obtained from an individual, including cell lines. The sample can also be partially processed from a sample directly obtained from an individual, e.g., cell lysate or blood depleted of red blood cells.

As used herein, the term "cellular sample" refers to any sample containing intact cells, such as cell cultures, bodily fluid samples or surgical specimens taken for pathological, histological, or cytological interpretation.

As used herein, the term "tissue sample" shall refer to a cellular sample that preserves the cross-sectional spatial relationship between the cells as they existed within the subject from which the sample was obtained. "Tissue sample" shall encompass both primary tissue samples (i.e. cells and tissues produced by the subject) and xenografts (i.e. foreign cellular samples implanted into a subject).

As used herein, "histochemical detection" refers to a process involving labeling a biomarker or other structures in a tissue sample with detection reagents in a manner that permits microscopic detection of the biomarker or other structures in the context of the cross-sectional relationship between the structures of the tissue sample. Examples include affinity histochemistry (AHC), immunohistochemistry (IHC), chromogenic in situ hybridization (CISH), fluorescent in situ hybridization (FISH), silver in situ hybridization (SISH), and hematoxylin and eosin (H&E) staining of formalin-fixed, paraffin-embedded tissue sections.

As used herein, "immunohistochemistry" (IHC) refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection).

Fluorescence (also frequently referred to as immunofluorescence) detection is a widely used IHC technique that can be either direct or indirect: direct indicates that primary antibodies are labeled with fluorescent probes and implies that there is no need to use fluorescent secondary antibodies, while indirect means that primary antibodies are unlabeled and secondary antibodies conjugated to fluorescent dyes have to be used for detection. Direct detection is the fastest and shortest IHC protocol, requiring incubation of tissue sections with only a primary antibody conjugated to the fluorophore of choice. Indirect detection is more sensitive than direct. The higher sensitivity of indirect detection is the result of the possibility of two secondary antibodies labeled with fluorophores interacting with a single molecule of primary antibody bound to its tissue target. Indirect detection allows for the ability to choose secondary antibodies with fluorophores of different colors, Stokes shifts, quantum yield, and fade resistance. Fluorescence detection allows for simultaneous detection of multiple overlapping and non-overlapping tissue targets. Multicolor detection can be done using either direct or indirect detection, or a combination of both techniques.

Counterstaining is the staining of tissue sections with dyes that allow one to see the entire "landscape" of the tissue section and serve as a reference for the main color used for the detection of tissue targets. Such dyes can stain cell nuclei, the cell membrane, or the entire cell. Examples of dyes include DAPI, which binds to nuclear DNA and emits strong blue light; Hoechst blue stain, which binds to nuclear DNA and emits strong blue light; and Propidium iodide, which binds to nuclear DNA and emits strong red light. Counterstaining of the intracellular cytoskeletal network can be done using phalloidin conjugated to fluorescent dyes. Phalloidin is a toxin that tightly binds to actin filaments in a cell's cytoplasm, which then become clearly visible under the microscope.

The majority of chromogenic IHC protocols are based on the use of Avidin and Biotin molecules because detection sensitivity of a simple antigen-antibody reaction in many cases is quite low. Avidin-Biotin binding serves to bridge antigen-bound antibodies with detection reagents, allowing amplification of the staining signal. The most frequently used Biotin-based techniques include labeled SA-Biotin (LSAB) and Avidin-Biotin Complex (ABC) detection. There are also non-Biotin-based detection techniques utilizing primary antibodies either conjugated directly to enzymatic labels or to a long polymer containing multiple copies of enzymatic labels.

LSAB Detection utilizes secondary antibodies conjugated to Biotin that link primary antigen-bound antibodies to SA conjugated to an enzyme. The first step in LSAB detection is the incubation of tissue sections with primary antibodies followed by incubation with biotinylated secondary antibodies. After that, SA conjugated to the enzyme of choice (e.g., AP, HRP, etc.) is added to tissue sections followed by adding appropriate enzyme substrate. The enzyme converts substrate into colored particles precipitating at the sites of antigen localization, which can then be observed under the microscope. LSAB technique can be shortened using biotinylated primary antibodies, eliminating the need for incubation with biotinylated secondary antibodies.

The initial steps—incubation with primary and biotinylated secondary antibodies—in ABC detection are the same as in LSAB, but the next steps and reagents are quite different. Avidin and biotinylated enzymes are first mixed and incubated together for about 30 min at room temperature and then added to tissue sections. During this incubation, Avidin interacts with the biotinylated enzymes, forming large complexes densely packed with enzyme molecules—far exceeding the concentration found in the LSAB detection technique—that boost the sensitivity of antigen detection.

Non-Biotin detection techniques have gained popularity because they are devoid of such limitations of Avidin-Biotin detection as nonspecific background staining due to the endogenous biotin that is abundant in different types of animal tissues, including kidney, brain, and placenta.

In chromogenic IHC, tissue counterstaining serves the same purpose as it does in fluorescence detection: to visualize the entire layout of the tissue section and label organelles of the same type. Usually counterstaining is done to label cell nuclei that should not be of the same color as the main color depicting antigens of interest. For example, if the main color is red (AEC chromogen) or brown (DAB chromogen), nuclei may be stained using Hematoxylin, which produces a blue color, or Methyl Green, which produces a green color. If the main color is blue (BCIP/NBT chromogen), then nuclei may be counterstained red using Nuclear Fast Red dye. In cases when tissue antigen is localized in cell nuclei, the duration of their counterstaining may be either shortened to make them barely visible or even skipped to avoid masking the main IHC color.

AHC refers to affinity histochemistry wherein detection of a biomarker involves the use of a binding agent with affinity for the biomarker. For example, mast cells may be stained by AHC based on electrostatic attractions between the basic protein avidin and the polyanionic heparin (identifiable by immunofluorescence).

As used herein, the term "section" shall refer to a thin slice of a tissue sample suitable for microscopic analysis, typically cut using a microtome. As an example, a section may be 4 to 5 microns thick. The present invention is not limited to 4 to 5 microns.

As used herein, the term "serial section" shall refer to any one of a series of sections cut in sequence from a tissue sample. For two sections to be considered "serial sections" of one another, they do not necessarily need to consecutive sections from the tissue, but they should generally contain the same tissue structures in the same cross-sectional relationship, such that the structures can be matched to one another after histological staining.

As used herein, the phrase "specific binding," "specifically binds to," or "specific for" refers to measurable and reproducible interactions such as binding between a target and a biomarker-specific agent, which is determinative of the presence of the target in the presence of a heterogeneous population of molecules including biological molecules. For example, a binding entity that specifically binds to a target is an antibody that binds this target with greater affinity, avidity, more readily, and/or with greater duration than it binds to other targets.

As used herein, the term "biomarker-specific agent" or "specific binding agent" shall refer to any compound or composition that binds to a biomarker or a specific structure within that biomarker in a manner that permits a specific detection of the biomarker in a sample. Examples include: antibodies and antigen binding fragments thereof; and engineered specific binding structures, including ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor; Amgen, Thousand Oaks, Calif.), dAbs (scaffold based on VH or VL antibody domain; GlaxoSmithKline PLC, Cambridge, UK), DARPins (scaffold based on Ankyrin repeat proteins; Molecular Partners AG, Zurich, CH), ANTI-CALINs (scaffold based on lipocalins; *Pieris* AG, Freising, DE), NANOBODYs (scaffold based on VHH (camelid Ig); Ablynx N/V, Ghent, BE), TRANS-BODYs (scaffold based on Transferrin; Pfizer Inc., New York, N.Y.), SMIPs (Emergent Biosolutions, Inc., Rockville, Md.), and TETRANEC-TINs (scaffold based on C-type lectin domain (CTLD), tetranectin; Borean Pharma A/S, Aarhus, DK) (Descriptions of such engineered specific binding structures are reviewed by Wurch et al., Development of Novel Protein Scaffolds as Alternatives to Whole Antibodies for Imaging and Therapy: Status on Discovery Research and Clinical Validation, Current Pharmaceutical Biotechnology, Vol. 9, pp. 502-509 (2008), the content of which is incorporated by reference); and fusion proteins including at least a first domain capable of specifically binding to the biomarker (e.g. an antigen binding fragment of an antibody or a target-binding portion of a protein that binds to the biomarker) and a second portion that is adapted to facilitate binding of detection reagents to the fusion protein (e.g., a biotin label, an epitope tag, an Ig fragment, etc.).

A "detection reagent" when used in connection with a histochemical assay (including immunohistochemistry and affinity histochemistry) is any reagent that is used to deposit a stain in proximity to a biomarker-specific agent bound to a biomarker in a cellular sample. Non-limiting examples include secondary antibodies capable of binding to a biomarker-specific antibody; enzymes linked to such secondary antibodies; and chemicals reactive with such enzymes to effect deposition of a fluorescent or chromogenic stain; and the like.

When used as a noun, the term "stain" shall refer to any substance that can be used to visualize specific molecules or structures in a cellular sample for microscopic analysis, including bright field microscopy, fluorescent microscopy, electron microscopy, and the like. When used as a verb, the term "stain" shall refer to any process that results in deposition of a stain on a cellular sample (e.g., tissue sample, cytological sample, etc.).

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Systems and Applications for the Present Invention

The present invention features compositions comprising a solid, dissolvable reagent composition for delivering said reagent (e.g., antibodies, probes, buffers, chromogens, counterstains, etc.) to a sample. The present invention also features methods of producing said compositions, methods (applications) of using said compositions (e.g., methods of introducing antibodies to a sample, etc.), and systems (e.g., automated systems) featuring the use of said compositions. For example, the present invention features methods, systems, and compositions for delivering a reagent to a sample, e.g., delivering an antibody to a tissue sample or tissue section adhered to a slide (e.g., for the detection of a biomarker).

In some embodiments, the systems or compositions of the present invention are used for histochemical applications, e.g., the delivery of antibodies or probes or other reagents to a tissue section, automated histochemical staining methods as described herein, etc. The present invention is not limited to histochemical applications. For example, in some embodiments, the systems or compositions of the present invention are used for other tests or assays, such as ELISAs, staining assays (e.g., for primary stains, special stains), or any other method or test or assay involving the application or a reagent such as a detection reagent, a binding reagent, a biomarker-specific agent, an enzyme, a protein, a nucleic acid, a stain, etc., wherein the reagent can be applied as a solid, dissolvable reagent.

In some embodiments, the systems or compositions of the present invention are used in manual methods. In some embodiments, the systems or compositions of the present invention are used in automated methods.

Automated Staining Machines

The solid, dissolvable reagents of the present invention may be used in an automated staining machine. The methods of the present invention may be performed on an automated staining machine (slide stainer) or other appropriate automated slide processing machine, e.g., a slide staining machine that utilizes puddle technology to deliver reagents. Specific examples of automated staining machines (e.g., IHC/ISH slide stainers) include: itelliPATH (Biocare Medical), WAVE (Celerus Diagnostics), DAKO OMNIS and DAKO AUTOSTAINER LINK 48 (Agilent Technologies), BENCHMARK XT (Ventana Medical Systems, Inc.), BENCHMARK ULTRA (Ventana Medical Systems, Inc.), BENCHMARK GX (Ventana Medical Systems, Inc.), VENTANA H&E 600 (Ventana Medical Systems, Inc.), BENCHMARK Special Stains (Ventana Medical Systems, Inc.), VENTANA DISCOVERY XT (Ventana Medical Systems, Inc.), VENTANA DISCOVERY ULTRA (Ventana Medical Systems, Inc.), Leica BOND, and Lab Vision Autostainer (Thermo Scientific). Automated staining machines (automated slide stainers) are also described by Prichard, Overview of Automated Immunohistochemistry, Arch Pathol Lab Med., Vol. 138, pp. 1578-1582 (2014), incorporated herein by reference in its entirety. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. The methods of the present invention may be adapted to be performed on any appropriate automated staining machine (or automated slide processing machine).

Automated IHC/ISH slide stainers typically include at least a stainer unit for dispensing reagent to implement staining protocols onto a slide. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity parallel to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In some variations of capillary gap staining, the reagents are mixed in the gap, such as translating gap technology, in which a gap is created between the slide and a curved surface and movement of the surfaces relative to one another effects mixing (see U.S. Pat. No. 7,820,381); and dynamic gap staining, which uses capillary forces similar to capillary gap staining to apply sample to the slide, and then translates the parallel surfaces relative to one another to agitate the reagents during incubation to effect reagent mixing (such as the staining principles implemented on DAKO OMNIS slide stainers (Agilent)). It has recently been proposed to use inkjet technology to deposit reagents on slides. See WO 2016-170008 A1. As an example, the VENTANA DISCOVERY ULTRA system features slide drawers with 30 independent slide reaction chambers with dedicated bulk reagent supply lines and individual slide heaters, a reagent carousel with 35 reagent positions, and the ability to hold up to 7 different bulk reagents in 3- to 6-liter onboard containers. The system has a slide temperature range from ambient temperature up to about 100° C. The BENCHMARK Special Stains system has a slide carousel for processing up to 20 slides with independent temperature control for each position, a reagent carousel with 25 reagents positions, and the ability to hold up to 4 bulk solutions in 3- to 6-liter onboard containers. The BenchMark ULTRA system can process up to 30 slides with independent processing/functionality and temperature control for each position. The system has a reagent carousel with 35 reagent positions and the ability to hold up to 7 different bulk reagents, which can be changed without process interruption. The system has a slide temperature range from ambient temperature up to about 100° C.

This list of staining principles is not intended to be exhaustive, and the present methods and systems are intended to include any staining technology (both known and to be developed in the future) that can be used to apply the appropriate reagents to the sample.

Samples

As previously discussed, the sample used in the methods and systems of the present invention may be compositions comprising cells or tissue, or purified or separated components of cells, tissues, or blood, e.g., DNA, RNA, proteins, cell-free portions, or cell lysates. The sample may be a formalin-fixed, paraffin-embedded (FFPE) tissue sample, e.g., from a tumor or metastatic lesion, e.g., primary tumor or metastatic tumor, a healthy sample, etc. The sample can also be from previously frozen or fresh tissue, or from a liquid sample, e.g., blood or a blood component (plasma or serum), urine, semen, saliva, sputum, mucus, semen, tear, lymph, cerebral spinal fluid, material washed from a swab, etc. In some embodiments, the sample in vitro cultures of cells obtained from an individual, including cell lines. In some embodiments, the sample is partially processed from a sample directly obtained from an individual, e.g., cell lysate or blood depleted of red blood cells.

In some embodiments, the samples used in the present invention are tissue samples or tissue sections, such as tissue sections adhered to a slide. However, the present invention is not limited to tissue samples, and the present invention is not limited to samples adhered to a slide. For example, in some embodiments, the sample is in a tube, a well (e.g., a multiwell plate), or other container. In some embodiments, the sample is a solid sample. In some embodiments, the sample is a liquid-based sample. In some embodiments, the sample comprises tissue or cells. In some embodiments, the sample comprises nucleic acid, protein, bacteria, viruses, or any other test agent.

As an example, a tissue sample may be of any type appropriate for histological examination on an automated staining machine (as described herein). The tissue sample may comprise a biopsy or surgical resection. The tissue sample may comprise a section of cancerous and/or healthy tissue. In some embodiments, the sample is fresh, frozen, formalin fixed paraffin embedded (FFPE), etc. In some embodiments, the tissue sample is fixed in order to preserve the shape of the cells or tissue. Common fixatives include formaldehyde, ethanol, methanol, and/or picric acid.

If the tissue sample is a sample embedded in paraffin, the sample can be deparaffinized with the automated IHC/ISH slide stainer using appropriate deparaffinizing fluid(s). After the waste remover removes the deparaffinizing fluid(s), any number of substances can be successively applied to the sample. The substances can be for pretreatment, cell lysis, denaturation, washing or the like.

Reagents

Reagents for immunohistochemistry or in situ hybridization include antibodies, buffers, stains, nucleic acids, enzymes, as well as other molecules such as tyramide or other detection reagents. The solid compositions (water-soluble polymer compositions) of present invention may include any of the aforementioned reagents. Non-limiting examples of antibodies (Ventana Medical Systems, Inc.) include: Estrogen Receptor (ER) (SP1) rabbit monoclonal primary antibody; EGFR (5B7) rabbit monoclonal primary antibody; FITC IgG primary antibody; c-MYC (Y69) rabbit monoclonal primary antibody; CD8 (SP57) rabbit monoclonal primary antibody, etc. Non-limiting examples of nucleic acids (Ventana Medical Systems, Inc.) includes: Chromosome 3 DIG probe; Chromosome 17 DIG probe; EGFR DNP Probe; HER2 Dual ISH DNA Probe cocktail; HPV6 mRNA probe; Kappa DNP probe; Lambda DNP probe; MYC DNP probe; etc. Non-limiting examples of other reagents (Ventana Medical Systems, Inc.) include: ISH Protease 1; Protease 3; hematoxylin; bluing reagent; hematoxylin II; blocking reagents; amplification reagents; etc.

Representative buffering agents or salts include, but are not limited to, Tris, Tricine, HEPES, MOPS, TAPS, Bicine, TAPSO, TES, PIPES, Cacodylate, SSC, MES, KCl, NaCl, potassium acetate, NH4-acetate, potassium glutamate, NH4Cl, ammonium sulphate, MgCl2, magnesium acetate and the like. Other agents that may be present in the buffer medium include chelating agents, such as EDTA, EGTA and the like.

Non-limiting examples of chromogen substrates that may be used in the solid reagents of the present invention include but are not limited to DAB, AEC, CN, BCIP/NBT, FAST RED, FAST BLUE, FUCHSIN, NBT, ALK, See also U.S. Pat. Publ. 2013/0260379 which is incorporated by reference herein in its entirety.

The aforementioned reagents are for exemplary purposes only and are not intended to limit the present invention to those reagents.

Solid Reagent Compositions

Any appropriate configuration of the solid reagent composition may be considered. While the present disclosure mentions solid reagent compositions in the form of wafers or films (a reagent embedded in wafers or films), packets (e.g., packets filled with a reagent), or reagent-printed films (e.g., a reagent inkjet printed onto films), the present invention is not limited to these configurations. Further, the solid reagent compositions of the present invention may be constructed from a variety of materials.

A. Films or Wafers

In certain embodiments, the solid reagent composition is in the form of a wafer or film, wherein the wafer or film comprises a water-soluble polymer and one or more reagents embedded therein. In some embodiments, the water-soluble polymer that makes up the wafer or film comprises polyvinyl alcohol (PVA), however the present invention is not limited to PVA. For example, in some embodiments, the water-soluble polymer comprises dextran, hydroxypropyl cellulose, poly (acrylic acid sodium salt), poly (ethylene glycol), poly (methylacrylic acid sodium salt), poly(styreneslfonic acid sodium salt), pullulan, maltodextrin, microcrystalline cellulose, maltodextrin, microcrystalline cellulose, PVA, the like, or a combination thereof. PVA is well known to one of ordinary skill in the art.

In certain embodiments, the water-soluble polymer further comprises a plasticizer, e.g., a formulation that helps improve flexibility of the film or wafer. Non-limiting examples of materials used as plasticizers include polytheylene glycols, glycerol, low molecular weight polyethylene glycols, phthalate derivatives (e.g., dimethyl phthalate, diethyl phthalate, dibutyl phthalate), citrate derivatives (e.g., tributyl citrate, triethyl citrate, acetyl citrate), triacetin, castor oil, etc.

Reagent films or wafers (e.g., PVA films, PVA wafers, etc.) may be constructed by dissolving water-soluble polymer (e.g., PVA) powder in a solvent. Non-limiting examples of solvents include ethanol-deionized (DI) water solutions (e.g., 50% ethanol-50% DI water, 60% ethanol-40% DI water, etc.), the like, or buffers, e.g., BenchMark ULTRA Reaction Buffer. Without wishing to limit the present invention to any theory or mechanism, it is believed that a buffer may be more beneficial for certain applications because it is safer to heat in order to dissolve the water-soluble polymer (e.g., PVA) quickly, and it also provides a stable environment for antibodies.

In certain embodiments, PVA wafers or films are constructed using PVA solutions (w/v). In certain embodiments, the PVA solution comprises 0.1% PVA (w/v). In certain embodiments, the PVA solution comprises 0.5% PVA (w/v). In certain embodiments, the PVA solution comprises 1% PVA (w/v). In certain embodiments, the PVA solution comprises 2% PVA (w/v). In certain embodiments, the PVA solution comprises 3% PVA (w/v). In certain embodiments, the PVA solution comprises 4% PVA (w/v). In certain embodiments, the PVA solution comprises 5% PVA (w/v). In certain embodiments, the PVA solution comprises 6% PVA (w/v). In certain embodiments, the PVA solution comprises 7% PVA (w/v). In certain embodiments, the PVA solution comprises 8% PVA (w/v). In certain embodiments, the PVA solution comprises 9% PVA (w/v). In certain embodiments, the PVA solution comprises 10% PVA (w/v). In certain embodiments, the PVA solution comprises from 0.1 to 1% PVA (w/v). In certain embodiments, the PVA solution comprises from 1 to 5% PVA (w/v). In certain embodiments, the PVA solution comprises from 0.1 to 10% PVA (w/v). In certain embodiments, the PVA solution comprises from 0.5 to 5% PVA (w/v). In certain embodiments, the PVA solution comprises from 2 to 5% PVA (w/v). In certain embodiments, the PVA solution comprises from 2 to 10% PVA (w/v).

The reagent or reagents are added to the water-soluble polymer (e.g., PVA) solutions. Subsequently, the reagent-water-soluble polymer (e.g., PVA) solutions are dehydrated, resulting in a reagent-embedded water-soluble polymer (e.g., PVA) film. In certain embodiments, water-soluble polymer (e.g., PVA) solutions are dehydrated at 37° C., 38° C., 39° C., 40° C., 41° C., 42° C., 43° C., 44° C., 45° C., etc. for a certain length of time.

B. Packets

In certain embodiments, the water-soluble polymer is in the form of a packet, wherein the packet comprises a water-soluble polymer with one or more reagents contained therein. In some embodiments, the water-soluble polymer that forms the packet comprises polyvinyl alcohol (PVA), however the present invention is not limited to PVA. For example, in some embodiments, the water-soluble polymer comprises dextran, hydroxypropyl cellulose, poly (acrylic acid sodium salt), poly (ethylene glycol), poly (methylacrylic acid sodium salt), poly(styreneslfonic acid sodium salt), pullulan, maltodextrin, microcrystalline cellulose, PVA, the like, or a combination thereof. PVA is well known to one of ordinary skill in the art.

In certain embodiments, the water-soluble polymer further comprises a plasticizer, e.g., a formulation that helps improve flexibility of the film or wafer. Non-limiting examples of materials used as plasticizers include polytheylene glycols, glycerol, low molecular weight polyethylene glycols, phthalate derivatives (e.g., dimethyl phthalate, diethyl phthalate, dibutyl phthalate), citrate derivatives (e.g., tributyl citrate, triethyl citrate, acetyl citrate), triacetin, castor oil, etc.

In certain embodiments, pre-made films of water-soluble polymer (e.g., PVA films) are used to create the packet. In certain embodiments, films of the water-soluble polymer (e.g., PVA films) are custom made.

As previously discussed, films (e.g., PVA films) may be constructed by dissolving water-soluble polymer (e.g., PVA) powder in a solvent. Non-limiting examples of solvents include ethanol-deionized (DI) water solutions (e.g., 50% ethanol-50% DI water, 60% ethanol-40% DI water, etc.), the like, or buffers, e.g., BenchMark ULTRA Reaction Buffer. As an example, in certain embodiments, PVA films are constructed using PVA solutions (w/v). In certain embodiments, the PVA solution comprises 0.1% PVA (w/v). In certain embodiments, the PVA solution comprises 0.5% PVA (w/v). In certain embodiments, the PVA solution comprises 1% PVA (w/v). In certain embodiments, the PVA solution comprises 2% PVA (w/v). In certain embodiments, the PVA solution comprises 3% PVA (w/v). In certain embodiments, the PVA solution comprises 4% PVA (w/v). In certain embodiments, the PVA solution comprises 5% PVA (w/v). In certain embodiments, the PVA solution comprises 6% PVA (w/v). In certain embodiments, the PVA solution comprises 7% PVA (w/v). In certain embodiments, the PVA solution comprises 8% PVA (w/v). In certain embodiments, the PVA solution comprises 9% PVA (w/v). In certain embodiments, the PVA solution comprises 10% PVA (w/v). In certain embodiments, the PVA solution comprises from 0.1 to 1% PVA (w/v). In certain embodiments, the PVA solution comprises from 1 to 5% PVA (w/v). In certain embodiments, the PVA solution comprises from 0.1 to 10% PVA (w/v). In certain embodiments, the PVA solution comprises from 0.5 to 5% PVA (w/v). In certain embodiments, the PVA solution comprises from 2 to 5% PVA (w/v). In certain embodiments, the PVA solution comprises from 2 to 10% PVA (w/v).

The water-soluble polymer (e.g., PVA) solutions are then dehydrated, resulting in a water-soluble polymer film (e.g., PVA film). In certain embodiments, water-soluble polymer (e.g., PVA) solutions are dehydrated at 37° C., 38° C., 39° C., 40° C., 41° C., 42° C., 43° C., 44° C., 45° C., etc. for a certain length of time.

The water-soluble polymer films (e.g., PVA films), whether custom made or pre-made, are configured to form an inner compartment for storing the reagent therein. For example, two (or more) water-soluble polymer films (e.g., PVA films) are melted together to form a packet with an opening for insertion of the reagent. In certain embodiments, several layers of water-soluble polymer films are stacked to form a portion (e.g., a side) of the packet. The reagent may be diluted in a solution that does not dissolve the water-soluble polymer. For example, in certain embodiments, the reagent (e.g., antibody) is diluted in glycerin. Once the reagent solution is added to the inner compartment of the packet, the packet is sealed (e.g., with heat).

C. Ink et Printed Films

In certain embodiments, the water-soluble polymer is in the form of a printed film (e.g., inkjet printed film), wherein the film comprises a water-soluble polymer with one or more reagents printed thereon.

In some embodiments, the film comprises polyvinyl alcohol (PVA), however the present invention is not limited to PVA. For example, in some embodiments, the water-soluble polymer comprises dextran, hydroxypropyl cellulose, poly (acrylic acid sodium salt), poly (ethylene glycol), poly (methylacrylic acid sodium salt), poly(styreneslfonic acid sodium salt), pullulan, PVA, the like, or a combination thereof. PVA is well known to one of ordinary skill in the art.

In certain embodiments, the water-soluble polymer further comprises a plasticizer, e.g., a formulation that helps improve flexibility of the film or wafer. Non-limiting examples of materials used as plasticizers include polytheylene glycols, glycerol, low molecular weight polyethylene glycols, phthalate derivatives (e.g., dimethyl phthalate, diethyl phthalate, dibutyl phthalate), citrate derivatives (e.g., tributyl citrate, triethyl citrate, acetyl citrate), triacetin, castor oil, etc.

In certain embodiments, pre-made films of water-soluble polymer (e.g., PVA films) are used for printing the reagent thereon. In certain embodiments, films of the water-soluble polymer (e.g., PVA films) are custom made.

As previously discussed, films (e.g., PVA films) may be constructed by dissolving water-soluble polymer (e.g., PVA) powder in a solvent. Non-limiting examples of solvents include ethanol-deionized (DI) water solutions (e.g., 50% ethanol-50% DI water, 60% ethanol-40% DI water, etc.), the like, or buffers, e.g., BenchMark ULTRA Reaction Buffer. As an example, in certain embodiments, PVA films are constructed using PVA solutions (w/v). In certain embodiments, the PVA solution comprises 0.1% PVA (w/v). In certain embodiments, the PVA solution comprises 0.5% PVA (w/v). In certain embodiments, the PVA solution comprises 1% PVA (w/v). In certain embodiments, the PVA solution comprises 2% PVA (w/v). In certain embodiments, the PVA solution comprises 3% PVA (w/v). In certain embodiments, the PVA solution comprises 4% PVA (w/v). In certain embodiments, the PVA solution comprises 5% PVA (w/v). In certain embodiments, the PVA solution comprises 6% PVA (w/v). In certain embodiments, the PVA solution comprises 7% PVA (w/v). In certain embodiments, the PVA solution comprises 8% PVA (w/v). In certain embodiments, the PVA solution comprises 9% PVA (w/v). In certain embodiments, the PVA solution comprises 10% PVA (w/v). In certain embodiments, the PVA solution comprises from 0.1 to 1% PVA (w/v). In certain embodiments, the PVA solution comprises from 1 to 5% PVA (w/v). In certain embodiments, the PVA solution comprises from 0.1 to 10% PVA (w/v). In certain embodiments, the PVA solution comprises from 0.5 to 5% PVA (w/v). In certain embodiments, the PVA solution comprises from 2 to 5% PVA (w/v). In certain embodiments, the PVA solution comprises from 2 to 10% PVA (w/v).

The water-soluble polymer (e.g., PVA) solutions are then dehydrated, resulting in a water-soluble polymer film (e.g., PVA film). In certain embodiments, water-soluble polymer (e.g., PVA) solutions are dehydrated at 37° C., 38° C., 39° C., 40° C., 41° C., 42° C., 43° C., 44° C., 45° C., etc. for a certain length of time.

The water-soluble polymer films (e.g., PVA films), whether custom made or pre-made, are used for printing one or more reagents thereon. In certain embodiments, inkjet printing is used to print the reagent(s) on the films. For example, solid water-soluble polymer films can be cut and placed onto an inject printer platform for printing. The present invention is not limited to inkjet printing.

Without wishing to limit the present invention to any theory or mechanism, it is believed that since the reagent is printed, the inkjet-printed antibody film does not require a particular liquid diluent (e.g., glycerin) to carry the antibody within the PVA. Further, the printing can be accomplished on just a single layer of water-soluble polymer (e.g., PVA), as opposed to two or more layers. A single layer of polymer will dissolve more readily during the assay.

EXAMPLES

Example 1—Process of Making Reagent-Embedded Wafers

Example 1 describes the production of several solid wafer reagents, e.g., one comprising Hematoxylin II, one comprising Bluing Reagent, etc. The present invention is not limited to the methods, compositions, and configurations described in Example 1.

Figure 1B:
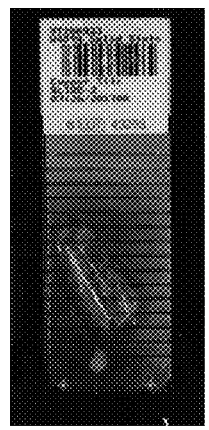
FIG. 1B shows dissolving of a reagent wafer when applied to a buffer on a slide.

PVA wafers were initially made by preparing a 2% or 5% PVA solution by dissolving PVA powder (Mw 89,000-98,000, 99+% hydrolyzed; Sigma Aldrich, P/N 341584) in 50% ethanol, and 50% deionized (DI) water. Additional wafers were made by dissolving PVA in BenchMark Ultra Reaction Buffer (P/N 950-300), which helped provide a stable environment for antibodies. For experiments described in this example, 2 g or 5 g of PVA powder, for 2% and 5% PVA solutions (w/v), respectively, was mixed with 100 mL of Reaction Buffer in a beaker, and stirred with a stir bar at 90-100° C. to facilitate dissolution until the solution was clear. 400 µL of each PVA solution was pipetted onto a clean polystyrene or ceramic tray to form a puddle, and a single slide dispense (100 µL) of each OptiView IHC detection kit (e.g., PTEN (SP218) Rabbit Monoclonal Primary Antibody (P/N 790-5097, Ventana Medical Systems, Tucson, Ariz.), Hematoxylin II (P/N 790-2208, Ventana Medical Systems, Tucson, Ariz.), or Bluing Reagent (P/N 760-2037, Ventana Medical Systems, Tucson, Ariz.)) or ancillary reagent being tested was dispensed directly onto the puddle of PVA solution (lx). The reagent-PVA solution was then dehydrated at 37° C. for 1-2 hours, resulting in a reagent-embedded PVA film (see FIG. 1A). FIG. 1B shows the wafer dissolved when applied to the reaction buffer puddle on a slide.

Example 2—Process of Making Antibody-Embedded Wafers

Example 2 describes the production of a solid reagent comprising an antibody, wherein the antibody is embedded into a wafer. The present invention is not limited to the methods, compositions, and configurations described in Example 2. For example, the present invention is not limited to embedding a reagent into a wafer or film, the use of an antibody, the use of PVA, etc.

Figure 2A:
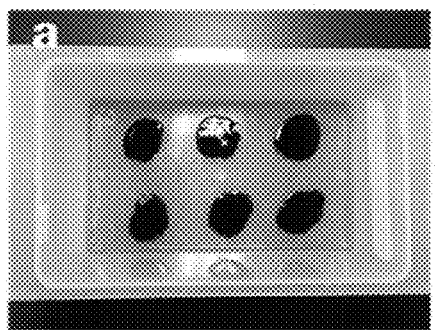
FIG. 2A is a photograph illustrating an antibody-PVA solution distributed in trays in 500 μL droplets for dehydration into a film.
Figure 2B:
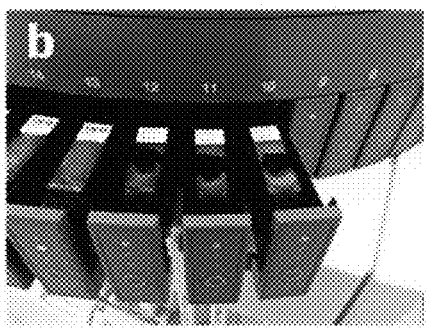
FIG. 2B is a photograph of slides containing the antibody-PVA thin film of FIG. 2A inserted into an automated slide stainer.

1-4% PVA solutions were made from PVA powder (Mw 89,000-98,000, 99+% hydrolyzed; Sigma Aldrich, P/N 341584), ethanol, and deionized (DI) water. 1-4 g of PVA powder, for 1% and 4% PVA solutions (w/v), respectively, was mixed with 40 mL of DI water and 60 mL of 100% ethanol in a beaker, and stirred with a stir bar at 80-90° C. to facilitate dissolution until the solution was clear. 400 µL of each PVA solution was pipetted into a clean tray to form a puddle, and a single slide dispense (100 µL) of PTEN (SP218) Rabbit Monoclonal Primary Antibody (P/N 790-5097, Ventana Medical Systems, Tucson, Ariz.) was dispensed directly onto puddle of PVA solution (lx). The antibody-PVA solution was then dehydrated at 45° C. resulted in an antibody embedded PVA film. FIG. 2A shows the antibody-PVA solution as distributed in trays in 500 µL droplets for dehydration into a film in an oven at 45° C. FIG. 2B shows a VENTANA BenchMark ULTRA automated stainer wherein the primary antibody hand titration option in the staining procedure is used to apply the solid reagent. Purple food coloring was added to the PVA for visualization purposes.

Example 3—Process of Making Antibody Packet

Example 3 describes the production of a solid reagent comprising an antibody, wherein a packet is filled with an antibody-glycerin solution. The present invention is not limited to the methods, compositions, and configurations described in Example 3. For example, the present invention is not limited to the use of antibodies, the use of PVA, a packet configuration, etc.

Figure 3A:
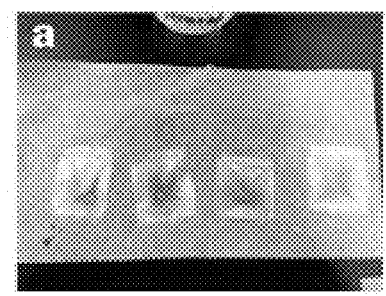
FIG. 3A is a photograph illustrating a PVA packet prototype filled with antibody diluted in glycerin.

A NSCLC sample slide was prepared according to standard protocols as known to one of skill in the art. Commercially available PVA film was purchased (SULKY of America; Item No. 486-12). The PVA film was cut into small squares approximately 4 cm×4 cm with scissors. Two squares were stacked and melted together with a soldering iron to form ¾ of a packet outline. A layer of wax paper was used to transfer heat. Raw PTEN (SP218) Rabbit Monoclonal Primary Antibody was diluted 1× (1:300) in glycerin (which would not dissolve the water soluble PVA). 100 μL of the antibody-glycerin solution was pipetted into the PVA packet. The packet was sealed closed with the soldering iron (see FIG. 3A). Red food coloring was added for visualization.

Figure 3B:
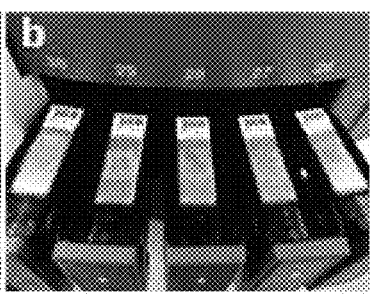
FIG. 3B is a photograph illustrating the packet prototype of FIG. 3A placed on an automated slide stainer.

Referring to FIG. 3B, the PVA packet filled with antibody diluted in glycerin (of FIG. 3A) was placed on slides on the VENTANA BenchMark ULTRA automated stainer (Ventana Medical Systems, Tucson, Ariz.) using the primary antibody hand titration option in the staining procedure. The puddle of reaction buffer on top of the slide dissolved the PVA, releasing the antibody and enabling staining with the primary antibody. Red food coloring was added for visualization.

Example 4—Process of Making Inkjet Printed Antibody Film

Example 4 describes the production of a solid reagent comprising an antibody, wherein the antibody is printed onto a film. The present invention is not limited to the methods, compositions, and configurations described in Example 4. For example, the present invention is not limited to manufacturing methods using printing, the use of an antibody, the use of PVA, etc.

Figure 4A:
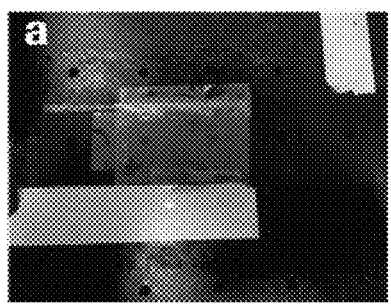
FIG. 4A is a photograph illustrating an inkjet-printed antibody on PVA film prototype mounted to the printing stage of the inkjet printer.
Figure 4B:
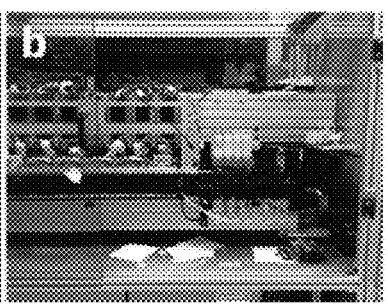
FIG. 4B is a photograph illustrating the inkjet printer used to print the prototype of FIG. 4A
Figure 5A:
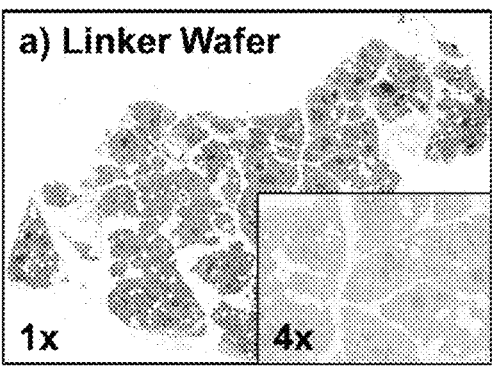
FIG. 5A is a 1× micrograph (with 4× zoom inset) illustrating normal pancreas tissue stained with PTEN (SP218) antibody from 2% PVA antibody embedded film applied during the Linker (secondary antibody) detection step.
Figure 5B:
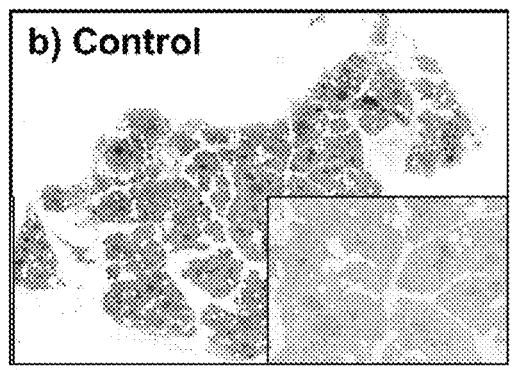
FIG. 5B is a 1× micrograph (with 4× zoom inset) illustrating normal pancreas tissue stained with PTEN (SP218) antibody with a dispenser for the Linker (secondary antibody) detection step as a control.
Figure 5C:
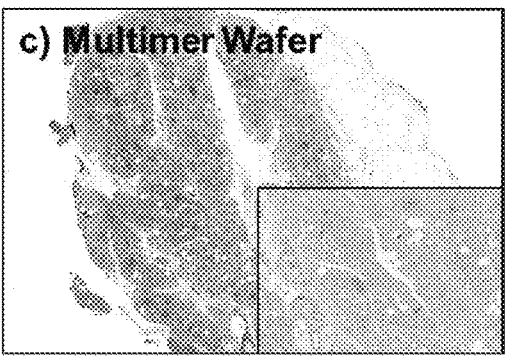
FIG. 5C is a 1× micrograph (with 4× zoom inset) illustrating normal pancreas tissue stained with PTEN (SP218) antibody from 2% PVA antibody embedded film applied during the Multimer (tertiary antibody) detection step.
Figure 5D:
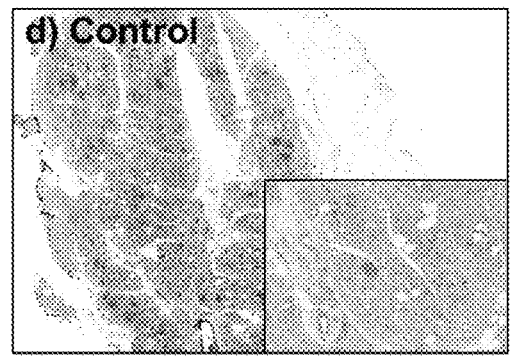
FIG. 5D is a 1× micrograph (with 4× zoom inset) illustrating normal pancreas tissue stained with PTEN (SP218) antibody with a dispenser for the Multimer (tertiary antibody) detection step as a control.
Figure 6A:
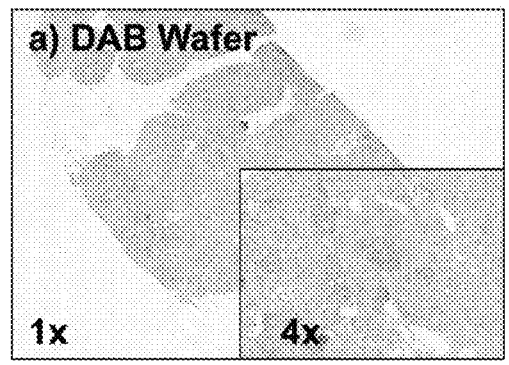
FIG. 6A is a 1× micrograph (with 4× zoom inset) illustrating normal pancreas tissue stained with PTEN (SP218) antibody from 2% PVA DAB embedded film applied during the DAB detection step.
Figure 6B:
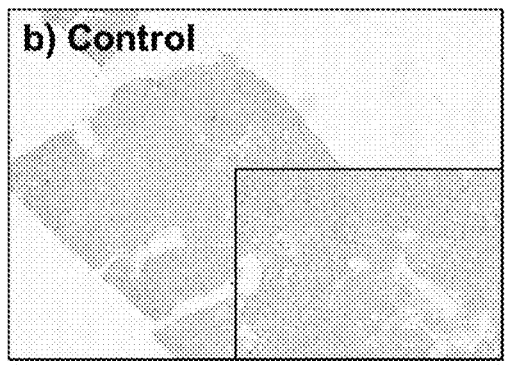
FIG. 6B is a 1× micrograph (with 4× zoom inset) illustrating normal pancreas tissue stained with PTEN (SP218) antibody with a dispenser for the DAB detection step as a control.
Figure 6C:
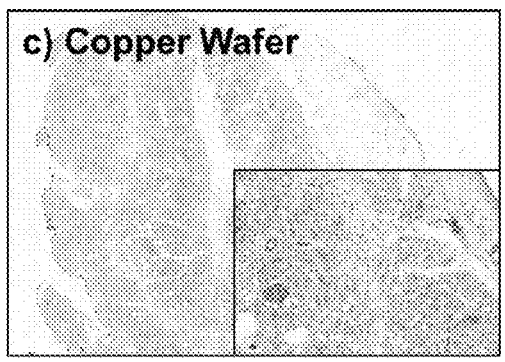
FIG. 6C is a 1× micrograph (with 4× zoom inset) illustrating normal pancreas tissue stained with PTEN (SP218) antibody from 2% PVA Copper Reagent embedded film applied during the Copper Reagent detection step.
Figure 6D:
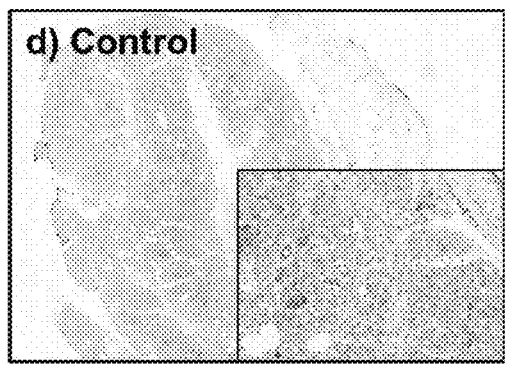
FIG. 6D is a 1× micrograph (with 4× zoom inset) illustrating normal pancreas tissue stained with PTEN (SP218) antibody with a dispenser for the Copper Reagent detection step as a control.
Figure 7A:
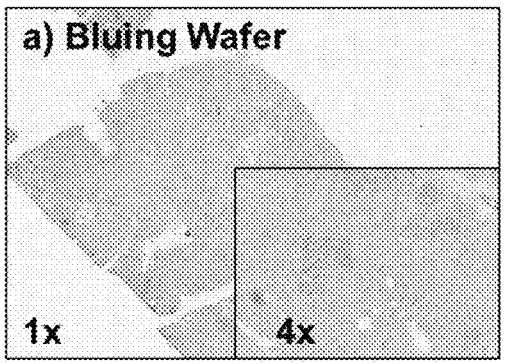
FIG. 7A is a 1× micrograph (with 4× zoom inset) illustrating normal pancreas tissue stained with PTEN (SP218) antibody from 2% PVA Bluing Reagent embedded film applied during the Bluing Reagent counterstain step.
Figure 7B:
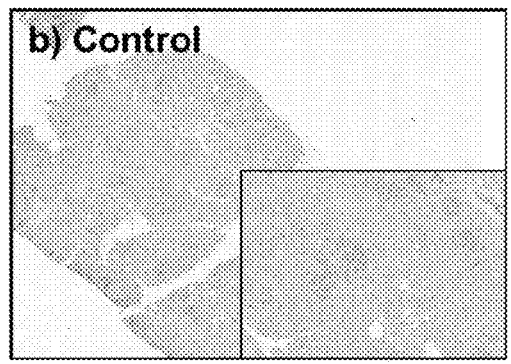
FIG. 7B is a 1× micrograph (with 4× zoom inset) illustrating normal pancreas tissue stained with PTEN (SP218) antibody with a dispenser for the Bluing Reagent counterstain step as a control.
Figure 7C:
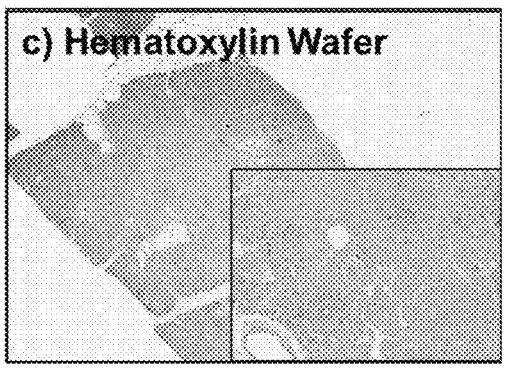
FIG. 7C is a 1× micrograph (with 4× zoom inset) illustrating normal pancreas tissue stained with PTEN (SP218) antibody from 2% PVA Hematoxylin II Reagent embedded film applied during the hematoxylin counterstain step.
Figure 7D:
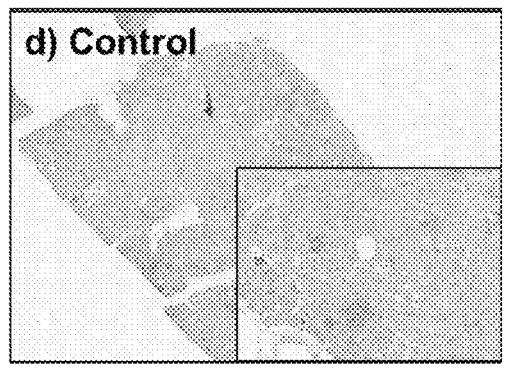
FIG. 7D is a 1× micrograph (with 4× zoom inset) illustrating normal pancreas tissue stained with PTEN (SP218) antibody with a dispenser for the hematoxylin counterstain step as a control.
Figure 8A:
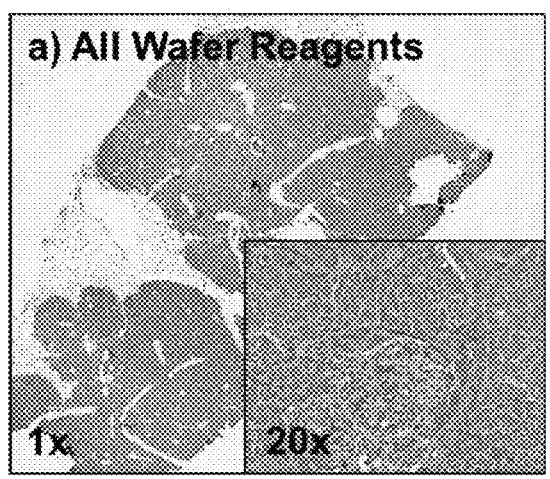
FIG. 8A is a 1× micrograph (with 20× zoom inset) illustrating normal pancreas tissue stained with PTEN (SP218) antibody using a primary antibody wafer, a linker wafer, a multimer wafer, a DAB wafer, a copper wafer, a bluing reagent wafer, and a hematoxylin wafer (made from 2% PVA in reaction buffer).
Figure 8B:
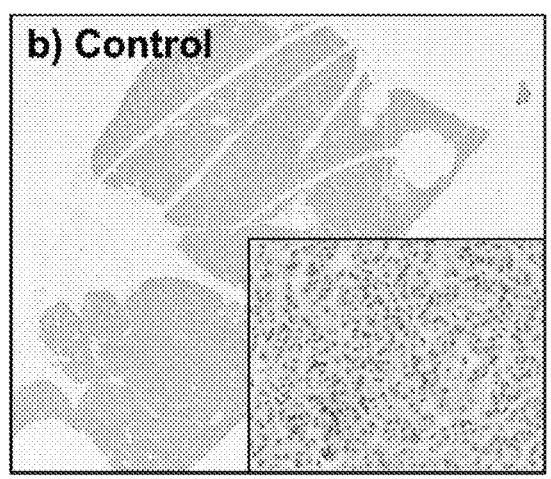
FIG. 8B is a 1× micrograph (with 20× zoom inset) illustrating normal pancreas tissue stained with PTEN (SP218) antibody with a dispenser for each antibody and reagent steps as a control.

Commercially available PVA film was purchased (SULKY of America; Item No. 486-12). PVA film was cut into small squares approximately 4 cm×4 cm, and placed onto the inkjet printer platform (FIG. 4A). Raw CD34 (QBEnd/10) Mouse Monoclonal Primary Antibody was diluted 200× (1:30) in Reaction Buffer, Glycerol, Tris-HCl and Brij-35 to simulate the antibody diluent. The antibody solution was loaded into inkjet cartridges and was printed onto the PVA film in a 1 in.×0.5 in. area at print density of 300 dpi to match the mass of antibody (1x) in a single slide dispense (FIG. 4B).

Example 5—Experimental Testing and Results for Reagent-Embedded Wafers

Example 5 describes testing of the reagent-embedded wafers of Example 1. The present invention is not limited to the methods, systems, and compositions described herein.

A. Procedure for Immunohistochemistry (IHC) Staining

Wafers made for each of the OptiView IHC and counterstain reagents (see Example 1) tested were stored at room temperature for less than 2 days prior to the functional testing with IHC staining runs. A customized staining procedure was created based on the staining procedure, "U OptiView DAB IHC v5.2 CDx" on a BenchMark ULTRA using the selections listed in Table 1 for the PTEN (SP218) primary antibody and Negative Reagent Control. The staining procedure was altered to allow for manual application "hand-apply" steps for the manual application of the reagent wafers being tested.

TABLE 1

Staining protocol selections used for functional testing of the prototypes on the BenchMark ULTRA using the U OptiView DAB IHC v5.2 CDx procedure

| PROCEDURE STEP | PTEN (SP218) | NEGATIVE REAGENT CONTROL |
| --- | --- | --- |
| Deparaffinization | Selected | Selected |
| Cell Conditioning (CC1) | 100° C., 56 minutes | 100° C., 56 minutes |
| Pre antibody peroxidase inhibitor | Selected | Selected |
| Antibody Incubation | 16 minutes, 37° C. | 16 minutes, 37° C. |
| OptiView HQ Linker | 8 minutes (default) | 8 minutes (default) |
| OptiView HRP Multimer | 8 minutes (default) | 8 minutes (default) |
| Hematoxylin II | 4 minutes | 4 minutes |
| Bluing Reagent | 4 minutes | 4 minutes |

Referring to Table 1, unstained slides of normal human pancreas tissues were placed in BenchMark ULTRA instruments and stained with PTEN (SP218) rabbit monoclonal primary antibody or rabbit monoclonal negative control Ig. The PVA film prototypes were placed manually onto the slide during the "hand apply antibody titration" step, where the instrument allows the user to open the slide drawer to manually apply antibody into the reaction buffer puddle on top of the slide. Controls for each run were included, where a normal dispenser was used to dispense the antibody onto the slide instead of the PVA prototype. Reaction buffer was also pipetted on top of the PVA film (approximately 400 μL) in order to compensate for buffer displaced by placement of the prototype, and to speed up PVA dissolution. Although this reaction buffer step was performed manually, it could be added to the staining procedure by changing the hand apply software macro to include a reaction buffer "adjust" step after closing the slide drawer. After each staining run, the slides were dehydrated and coverslipped according to the OptiView DAB Detection Kit package insert (1010323EN).

B. Results for Reagent-Embedded Wafer Compositions

Referring to FIG. 5, FIG. 6, FIG. 7, and FIG. 8, reagent-embedded PVA film wafers were used to stain normal pancreas tissues with PTEN (SP218) rabbit monoclonal antibody. Each detection reagent tested (Linker, Multimer, DAB, Copper, Hematoxylin and Bluing Reagent) was tested individually and then ultimately combined for an all-wafer staining run (see FIG. 8). Each run resulted in successful DAB detection of the PTEN (SP218) antibody, and counterstain. The staining results were consistent to the dispenser controls for the Linker, Multimer, DAB and Copper wafers (see FIG. 5, FIG. 6). Although Bluing Reagent and Hematoxylin wafers did result in successfully staining the tissue with counterstain, the staining quality was not comparable to the dispenser controls. Further optimization is needed to obtain acceptable staining quality (see FIG. 7).

Example 6—Experimental Testing and Results for Antibody-Embedded Wafers, Antibody Packets, and Inkjet Printed Antibody Films Example 6 describes testing of the solid reagents, e.g., antibody-embedded wafers, antibody packets, and inkjet printed antibody films, of Example 2, Example 3, and Example 4, respectively. The present invention is not limited to the methods, systems, and compositions described herein.

A. Procedure for Immunohistochemistry (IHC) Staining

Each of the three prototypes described in Example 2, Example 3, and Example 4 were stored at 4° C. for less than 5 days prior to the functional testing with IHC staining runs.

Staining protocols were created using the staining procedure, "U OptiView DAB IHC v5.2 CDx" on a BenchMark ULTRA automated stainer using the selections listed in Table 1 for the PTEN (SP218) and CD34 primary antibodies.

TABLE 2

Staining protocol selections used for functional testing of the prototypes on the BenchMark ULTRA using the U OptiView DAB IHC v5.2 CDx procedure

| PROCEDURE STEP | PTEN (SP218) | CD34 (QBEnd/10) |
| --- | --- | --- |
| Deparaffinization | Selected | Selected |
| Cell Conditioning (CC1) | 100° C., 56 minutes | none |
| Pre antibody peroxidase inhibitor | Selected | Selected |
| Antibody Incubation | Hand Titration Selected, 16 minutes, 37° C. | Hand Titration Selected, 16 minutes, 37° C. |
| OptiView HQ Linker | 8 minutes (default) | 8 minutes (default) |
| OptiView HRP Multimer | 8 minutes (default) | 8 minutes (default) |
| Hematoxylin II | 4 minutes | 4 minutes |
| Bluing Reagent | 4 minutes | 4 minutes |

Referring to Table 2, unstained slides of normal human prostate or placenta tissues were placed in BenchMark ULTRA instruments and stained with PTEN (SP218) and CD34 (QBEnd/10), respectively. The PVA film prototypes were placed manually onto the slide during the "hand apply antibody titration" step, where the instrument allows the user to open the slide drawer to manually apply antibody into the reaction buffer puddle on top of the slide. Controls for each run were included, where a normal dispenser was used to dispense the antibody onto the slide instead of the PVA prototype. Reaction buffer was also pipetted on top of the PVA film (approximately 400 µL) in order to compensate for buffer displaced by placement of the prototype, and to speed up PVA dissolution. Although this reaction buffer step was performed manually, it could be added to the staining procedure by changing the hand apply software macro to include a reaction buffer "adjust" step after closing the slide drawer. After each staining run, the slides were dehydrated and coverslipped according to the VENTANA OptiView DAB Detection Kit package insert (1010323EN, Ventana Medical Systems, Tucson, Ariz.)).

B. Results for Antibody Embedded Wafer Composition

Figure 9A:
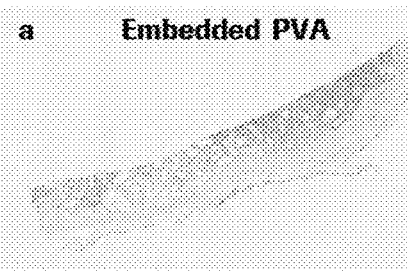
FIG. 9A is a micrograph illustrating normal prostate tissue stained with PTEN (SP218) antibody using 1% PVA antibody embedded film during the PTEN (SP218) primary antibody step.
Figure 9B:
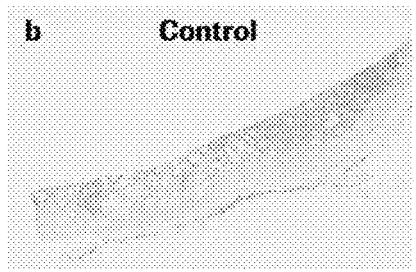
FIG. 9B is a micrograph illustrating normal prostate tissue stained with PTEN (SP218) antibody using a dispenser as a control.
Figure 9C:
FIG. 9C is a micrograph illustrating 40× magnification of the image of FIG. 9A.
Figure 9D:
FIG. 9D is a photograph illustrating 40× magnification of the image of FIG. 9B.

Referring to FIG. 9A, FIG. 9B, FIG. 9C, and FIG. 9D, the antibody embedded PVA film wafer was made with the proper concentrations of diluent components by adding the antibody to the PVA solution directly from a dispenser. In addition, formulating the PVA film promoted preliminary optimization of film composition. FIG. 9A illustrates a normal prostate tissue stained with PTEN(SP218) antibody from 1% PVA antibody embedded film while FIG. 9B illustrates normal prostate tissue stained with PTEN(SP218) antibody dispenser as a control. The slides in FIGS. 9A and 9B were comparably stained. FIG. 9C is a 40× magnification of the slide of FIG. 9A while FIG. 9D is a 40× magnification of the slide of FIG. 9B. Staining from each of the 1-4% PVA film wafers were consistent with the dispenser control; however, the 3% and 4% PVA films did not fully dissolve during the staining run, and remnants were found at the base of the slide after the staining run was complete. Dehydration of the antibody-PVA solution at 45° C. did not appear to affect antibody stability or function. On the other hand, dehydration at 60° C. led to antibody denaturation and loss of functional staining. Dehydration at lower temperatures, or even lyophilization, may improve stability and improve antibody function if some antibodies are found to be sensitive to heat.

C. Results for Antibody Packet Composition

Figure 10A:
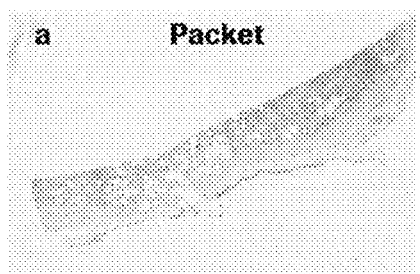
FIG. 10A is a micrograph illustrating normal prostate tissue stained with PTEN (SP218) antibody using PVA packet filled with glycerin and antibody.
Figure 10B:
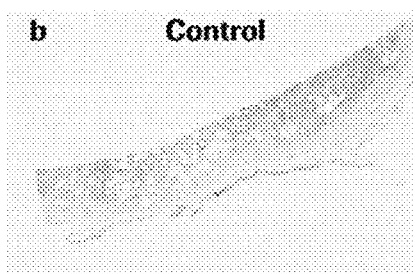
FIG. 10B is a micrograph illustrating normal prostate tissue stained with PTEN (SP218) antibody using a dispenser as a control.
Figure 10C:
FIG. 10C is a micrograph illustrating 40× magnification of the image of FIG. 10A.
Figure 10D:
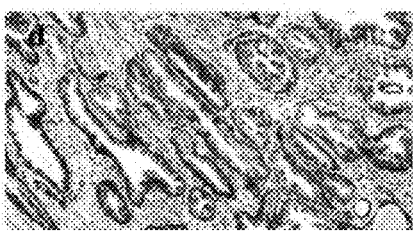
FIG. 10D is a micrograph illustrating 40× magnification of the image of FIG. 10B.

Initial staining from the antibody packet was inconsistent, and staining was improved when packets were made thinner and more reaction buffer was added to help dissolve the packet. However, staining intensities across the tissues remained inconsistent with small non-staining areas. FIG. 10A, FIG. 10B, FIG. 10C, and FIG. 10D illustrate examples of tissues stained with the PVA packet compared to a dispenser control. FIG. 10A is an image of normal prostate tissue stained with PTEN(SP218) antibody using PVA packet filled with glycerin and antibody while FIG. 10B is an image of normal prostate tissue stained with PTEN (SP218) antibody using a dispenser as a control (FIG. 10B). FIG. 10C illustrates 40× images of the packet while FIG. 10D illustrates 40× images of the control, revealing similar staining quality. Glycerin appeared to sink to bottom of the puddle as it was released from the dissolving PVA film during the hand apply step, which may have prevented the antibody from reaching the tissue and binding appropriately across the entire slide. Air bubbles were also observed when the packet was dissolving, and could also be blocking antibody from reaching some areas. Glycerin was chosen as a diluent for testing as it is readily commercially available, non-hazardous, and would not dissolve the surrounding PVA packet like aqueous antibody diluent. Glycerin is highly viscous liquid that does not readily dissolve in aqueous solutions, and has a higher density than water.

D. Results for Inkjet Printed Antibody Film Composition

FIG. 11A, FIG. 11B, FIG. 11C, and FIG. 11D show examples of tissues stained with the inkjet-printed antibody film compared to a dispenser control. Specific staining intensities from the inkjet-printed antibody film was consistent with the dispenser control; however, more background, or nonspecific, staining was present. Background staining may be attributed to different concentrations of diluent components that could be optimized with future studies.

FIG. 11A illustrates normal placenta tissue stained with CD34 (QBEnd/10) primary antibody printed onto PVA film while FIG. 11B illustrates normal placenta tissue stained with CD34 (QBEnd/10) primary antibody delivered with a dispenser as a control. FIG. 11C is a 40× magnification of the slide of FIG. 11A while FIG. 11D is a 40× magnification of the slide of FIG. 11B. These slides reveal similar stain intensity and slightly higher background staining with the PVA film. Specific staining intensities from the inkjet-printed antibody film were consistent with the dispenser control; however, more background, or nonspecific, staining was present. Background staining may be attributed to different concentrations of diluent components.

Example 7

Example 7 describes an example of a Staining Protocol for use with solid compositions of the present invention. The solid compositions used in the example below include a solid composition comprising a first (primary) antibody, a solid composition comprising a second antibody, a composition comprising a third antibody, a composition comprising a first detection reagent, a composition comprising a second detection reagent, a composition comprising hematoxylin, and a composition comprising a bluing reagent. The present invention is not limited to the methods, compositions, reagents, systems, or specific procedures described herein.

Apply deparaffinization solution
Apply antigen retrieval solution
Apply primary antibody solid composition
Apply secondary antibody solid composition
Apply third antibody solid composition
Apply first detection reagent solid composition
Apply second detection reagent solid composition
Apply Hematoxylin solid composition
Apply Bluing Reagent solid composition

REFERENCES

The disclosures of the following articles and patent documents are incorporated in their entirety by reference herein:

Butler J. E. "Solid Supports in Enzyme-Linked Immunosorbent Assay and Other Solid-Phase Immunoassays" Methods 22 (2000):4-23

De Melo-Junior M. R., Alves L. C., dos Santos F. B., Beltrao E. I. C., de Carvalho Jr L. B. "Polysiloxane-polyvinyl alcohol discs as support for antibody immobilization: Ultra-structural and physical-chemical characterization" React Funct Polym 68 (2008):315-320

Kennedy S. P., inventor; The Procter & Gamble Company, assignee. "Liquid Laundry Detergent in Water-Soluble Package". U.S. Pat. No. 4,973,416. Nov. 27, 1990

McWilliam, I., M. Chong Kwan, and D. Hall. "Inkjet Printing for the Production of Protein Microarrays." Methods in Molecular Biology 785 (2011): 345-61.

Robert, M C., M. Frenette, and C. Zhou. "A Drug Delivery System for Administration of Anti-TNF-α Antibody." Transnational Vision Science & Technology 5.2 (2016)

Sonenstein G. G., inventor; Colgate-Palmolive Company, assignee. "Water Soluble Films Of Polyvinyl Alcohol And Polyacrylic Acid And Packages Comprising Same". U.S. Pat. No. 4,692,494. Sep. 8, 1987

Stephens C, Suriyavirun N, inventors; Ventana Medical Systems, assignee. "Solid Single-dose Antibody and Reagent Delivery Method for IHC/ISH Instruments" U.S. Provisional Patent Application No. 62/437,545 Filed December 2016.

Wan T., Stylios G. K., Giannoudi M., Giannoudis P. V. "Investigating a new drug delivery nano composite membrane system based on PVA/PCL and PVA/HA(PEG) for the controlled release of biopharmaceuticals for bone infections." Injury, Int. J. Care Injured 46 S8 (2015):S39-S43

Various modifications of the invention, in addition to those described herein, will be apparent to those skilled in the art from the foregoing description. Such modifications are also intended to fall within the scope of the appended claims.

What is claimed is:

1. A method of depositing a reagent onto a sample, the method comprising:
(a) introducing the sample to an automated system, wherein the automated system comprises:
(i) a base for supporting the sample;
(ii) a liquid dispenser containing a liquid; and
(iii) a solid reagent dispenser containing a solid composition, wherein the solid composition comprises a water-soluble polymer and a reagent embedded in the water-soluble polymer, wherein the reagent is an antibody, an antibody fragment, or a protein, and wherein the water-soluble polymer comprises polyvinyl alcohol (PVA), dextran, hydroxypropyl cellulose, poly (acrylic acid sodium salt), poly (ethylene glycol), poly (methylacrylic acid sodium salt), poly (styrenesulfonic acid sodium salt), pullulan, or a combination thereof, and wherein the sample is placed on the base; and
(b) activating the automated system such that the liquid dispenser aliquots the liquid onto the sample and the solid reagent dispenser deposits the solid composition on top of the sample; and
wherein when the composition is deposited on top of the sample and the solid composition comes in contact with the liquid, the solid composition dissolves onto the sample, thereby depositing the reagent onto the sample.

2. The method of claim 1, wherein the sample comprises a tissue section.

3. The method of claim 1, wherein the liquid dispenser of the system aliquots the liquid onto the sample before the solid composition is deposited onto the sample.

4. The method of claim 1, wherein the liquid dispenser of the system aliquots the liquid onto the sample after the solid composition is deposited onto the sample.

5. The method of claim 1, wherein the water-soluble polymer is a film.

6. The method of claim 1, wherein the reagent is embedded in the water soluble polymer by infusing the reagent in the water-soluble polymer.

7. The method of claim 1, wherein the reagent is embedded in the water-soluble polymer by printing the reagent on the water-soluble polymer.

8. The method of claim 1, wherein the reagent is embedded in the water-soluble polymer by encapsulating the reagent with the water-soluble polymer.

9. The method of claim 1, wherein the solid composition further comprises a second reagent embedded in the water-soluble polymer, wherein the second reagent is selected from a group consisting of: an antibody, an antibody fragment, a protein, a nucleic acid, a chromogen, a stain, a counterstain, a lipid, a carbohydrate, an enzyme, a buffer, or a combination thereof.

* * * * *